(12) United States Patent
Kaal et al.

(10) Patent No.: US 8,052,654 B2
(45) Date of Patent: Nov. 8, 2011

(54) AUTOMATICALLY DISABLED SYRINGE

(75) Inventors: Joseph Hermes Kaal, Morpeth (AU); Craig Stephen Thorley, Largs (AU); Damien Judd, Heathmont (AU)

(73) Assignee: Unitract Syringe Pty Ltd., West Perth, Western Australia (AU)

( * ) Notice: Subject to any disclaimer, the term of this patent is extended or adjusted under 35 U.S.C. 154(b) by 795 days.

(21) Appl. No.: 10/587,782

(22) PCT Filed: Jan. 28, 2005

(86) PCT No.: PCT/AU2005/000106
§ 371 (c)(1),
(2), (4) Date: Apr. 18, 2007

(87) PCT Pub. No.: WO2005/072797
PCT Pub. Date: Aug. 11, 2005

(65) Prior Publication Data
US 2008/0208143 A1 Aug. 28, 2008

(30) Foreign Application Priority Data
Jan. 28, 2004 (AU) ................................ 2004900363

(51) Int. Cl.
*A61M 5/00* (2006.01)

(52) U.S. Cl. ................. 604/209; 604/220; 604/224
(58) Field of Classification Search ............. 604/110, 604/208, 210, 218, 220, 224
See application file for complete search history.

(56) References Cited

U.S. PATENT DOCUMENTS

| 4,642,102 | A | | 2/1987 | Ohmori |
| 4,950,163 | A | | 8/1990 | Zimble |
| 5,084,017 | A | * | 1/1992 | Maffetone ............... 604/110 |
| 5,222,942 | A | * | 6/1993 | Bader .................... 604/110 |
| 5,328,476 | A | | 7/1994 | Bidwell |
| 5,562,623 | A | * | 10/1996 | Shonfeld et al. ......... 604/110 |
| 6,494,863 | B1 | * | 12/2002 | Shaw et al. ............. 604/110 |
| 7,331,934 | B2 | * | 2/2008 | Suresh et al. ........... 604/110 |
| 2001/0049506 | A1 | | 12/2001 | Schoenfeld et al. |

(Continued)

FOREIGN PATENT DOCUMENTS

ES 2031756 A6 12/1992

(Continued)

OTHER PUBLICATIONS

European Supplementary Search Report for European Patent Application No. 05700137.2-2319/1708770 (Apr. 9, 2010).

*Primary Examiner* — Jackie Ho
*Assistant Examiner* — Brandy C Scott
(74) *Attorney, Agent, or Firm* — LeClairRyan, a Professional Corporation

(57) ABSTRACT

A syringe (10) has a plunger (20), a barrel (11) and a collar (40, 50) with two pawls (42A, 42B). The plunger has two opposed ratchets (23A, 23B) that align with the one each of the pawls and thereby or impede, withdrawal of the plunger during or following depression of the plunger. The barrel has a collar with an inner (50) and an outer member (40) that are incapable of rotation relative with respect to each other. The outer member has the two pawls (42A, 42B) and two fingers that slidably engage opposed guide slots (28) on the plunger to thereby prevent or minimize rotation of the plunger relative to the collar. The inner member of the collar is operable to prevent engagement of the plunger ratchet by the two pawls until the plunger is depressed.

28 Claims, 6 Drawing Sheets

FOREIGN PATENT DOCUMENTS

| | | |
|---|---|---|
| FR | 2639832 A1 | 12/1988 |
| FR | 2639832 A1 | 6/1990 |
| GB | 2 203 047 A | 10/1988 |
| WO | WO 89/12476 A1 | 12/1989 |
| WO | 9011790 A1 | 10/1990 |
| WO | WO 94/13339 A1 | 6/1994 |

\* cited by examiner

AUTOMATICALLY DISABLED SYRINGE

This application is a national stage application under 35 U.S.C. §371 from PCT Application No. PCT/AU2005/000106, filed Jan. 28, 2005, which claims the priority benefit of Australian Patent Application No. 2004900363, filed Jan. 28, 2004.

FIELD OF THE INVENTION

THIS INVENTION relates to syringes. More particularly, this invention relates to a syringe that includes an automatic mechanism to prevent or minimize the potential for re-use of the syringe.

BACKGROUND OF THE INVENTION

The practice of sharing syringes without adequate sterilization between successive users is a major contributor to the transfer of Human Immunodeficiency Virus (HIV), Hepatitis and other communicable diseases with subsequent severe repercussions for the sufferer and at a high cost to society for supporting and providing medical attention to sufferers.

In response to this problem, syringes have been developed with the aim of preventing syringe re-use.

One solution has been to develop syringes where the needle is permanently retractable into the barrel of the syringe, retraction driven by a compressed spring, as for example described in International Publication WO 01/80930.

Although very effective, retractable syringes are relatively expensive, particularly when required in large quantities for mass immunizations or for distribution to intravenous drug users. This is particularly a problem in third world countries where the incidence of HIV is high, mass immunization programs need to be frequently undertaken and healthcare resources are limited.

Several simpler and less expensive non-retractable syringe alternatives exist, such as syringes having disabling mechanisms that prevent re-use, but generally these syringes require the user to actively disable the syringe. Even health care professionals can at times be remiss and fail to actively disable such syringes after use.

It is therefore an object of the invention to overcome or alleviate at least one of the deficiencies of the prior art, or at least provide a useful alternative.

SUMMARY OF THE INVENTION

The present invention in one broad form provides a mechanism for a syringe which can automatically disable the syringe and thereby prevent re-use of the syringe, which mechanism is relatively simple and inexpensive to manufacture.

The present invention in another broad form provides a mechanism for a syringe which can automatically disable the syringe and thereby prevent re-use of the syringe, which mechanism can preferably be utilized with a non-retractable syringe needle.

In a first aspect, the invention provides a plunger for a syringe having at least one pawl for engaging said plunger, said plunger comprising at least one longitudinal ratchet capable of engaging said at least one pawl to thereby prevent withdrawal of said plunger during or following depression of said plunger.

In a second aspect, the invention provides a disabling system for a syringe, said disabling system comprising a plunger having at least one ratchet and a collar mountable to a barrel of said syringe, said collar comprising an inner member and an outer member having at least one pawl capable engaging said ratchet, said inner member operable to prevent engagement of said ratchet by said at least one pawl until said plunger is depressed.

In a third aspect, the invention provides a syringe comprising a plunger and a barrel having at least one pawl, said plunger comprising at least one longitudinal ratchet capable of engaging said at least one pawl to prevent withdrawal of said plunger during depression of said plunger.

In a preferred embodiment the invention provides a syringe comprising:
 (i) a barrel that comprises two pawls; and
 (ii) a plunger comprising:
  (a) two opposed ratchets respectively engageable by said two pawls to prevent withdrawal of said plunger during or following depression of said plunger; and
  (b) two opposed guide slots;
wherein said barrel comprises a collar having an inner member and an outer member that are incapable of rotation relative to each other, said inner member operable to prevent engagement of said ratchet by said two pawls until said plunger is depressed, said outer member comprising said two pawls and further comprising two fingers that respectively slidably engage said opposed guide slots of said plunger to thereby prevent rotation of said plunger relative to said collar.

In a fourth aspect, the invention provides a method of operating a syringe having a plunger and at least one pawl engageable with said plunger, said method including the step of depressing said plunger from a first position at which said at least one pawl is not engageable with said plunger to a second position at which said at least one pawl is engageable with said plunger and thereby prevents withdrawal of said plunger.

In a preferred embodiment, said plunger comprises two opposed ratchets, each disposed longitudinally along said plunger.

According to this embodiment, said collar comprises two pawls, each said pawl engageable with a respective said opposed ratchet to prevent withdrawal of said plunger during or following depression of said plunger.

The longitudinal ratchet may comprise a plurality of aligned steps, teeth, abutments or ridges oriented relative to said one or more pawls so as to be capable of engaging said one or more pawls, in use to prevent, impede or otherwise hinder withdrawal of said plunger during or following depression of said plunger.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to drawings wherein.

DETAILED DESCRIPTION OF THE INVENTION

Figure 1:
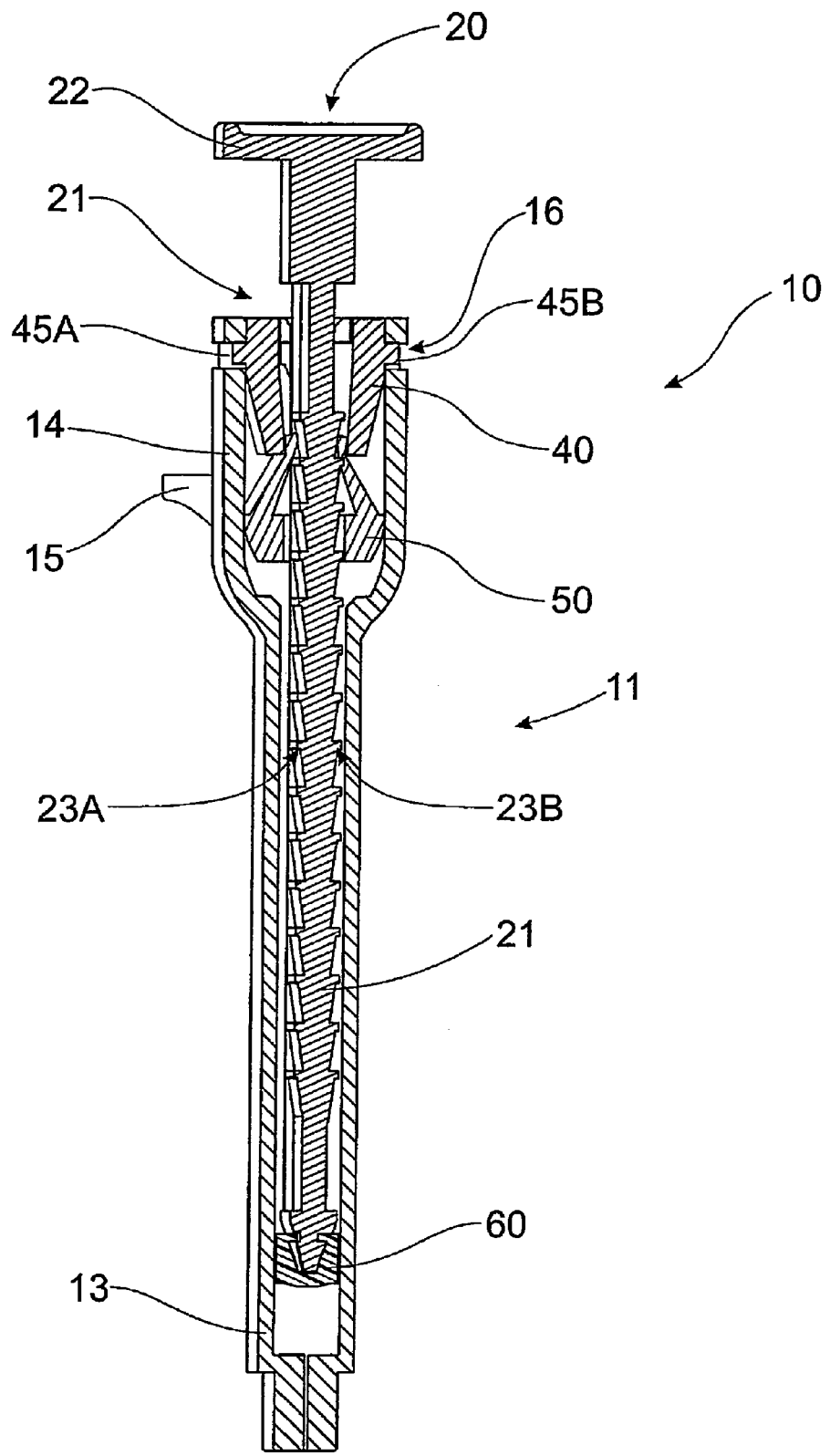
FIG. 1 is a perspective view of a longitudinal section through an embodiment of a syringe.

Referring to FIG. 1, syringe 10 comprises barrel 11 and plunger 20. Barrel 11 comprises needle end 13 to which is mountable a needle (not shown). Barrel 11 also comprises flared end 14 at which are located paired finger grips 15 and locating slots 16 in which is mounted barrel-engaging shoulders 45A, 45B of outer member 40. Inner member 50 is shown initially engaged with outer member 40. Barrel 11 may be of any capacity, although preferably barrel 11 is suitable for a syringe of less than 1.0 mL capacity, for example a 0.5 mL syringe. Plunger 20 comprises rod 21 with button 22 operable by a user, and opposed ratchets 23A, 23B, each disposed longitudinally along plunger rod 21.

Figure 2:
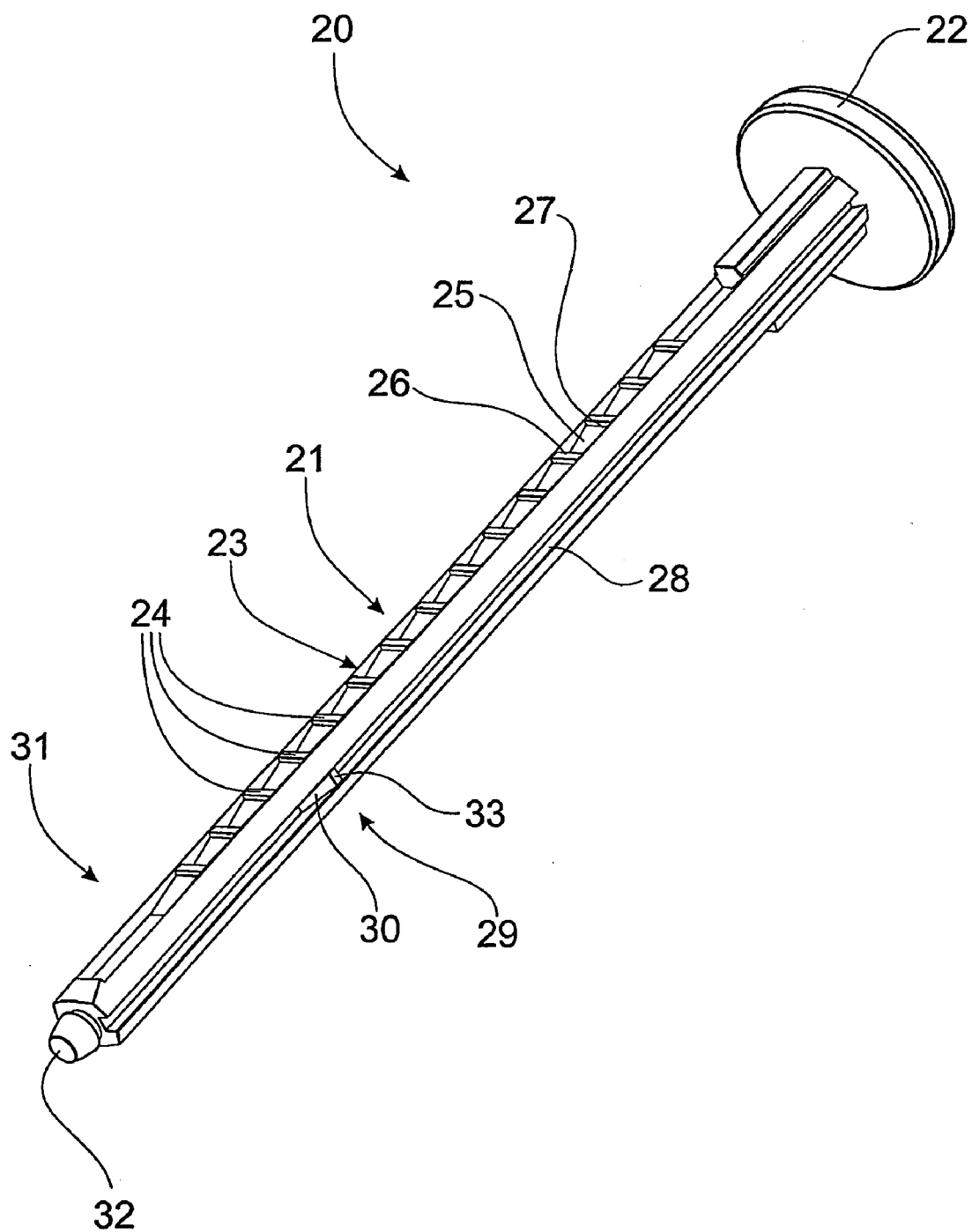
FIG. 2 is a perspective view of an embodiment of a plunger.

Referring to FIG. 2, each ratchet 23 comprises a plurality of steps 24. Each step 24 has deep shoulder 26 and shallow shoulder 27. There is also an inclined surface 25 intermediate adjacent steps 24.

Plunger rod 21 further comprises opposed guide slots 28, each of which comprises ramped abutment 29 each comprising ramp 30 and ledge 33. Guide slots assist maintaining a correct orientation of plunger 20 in use, while ledges 33 prevent complete withdrawal of plunger 20 from barrel 11, as will be described in more detail hereinafter. Ramps 30 assist in assembling plunger 20 into barrel 11.

Needle end 31 of plunger 20 comprises nub 32 which fits into seal 60, as can be more readily seen in FIG. 1.

Figure 3:
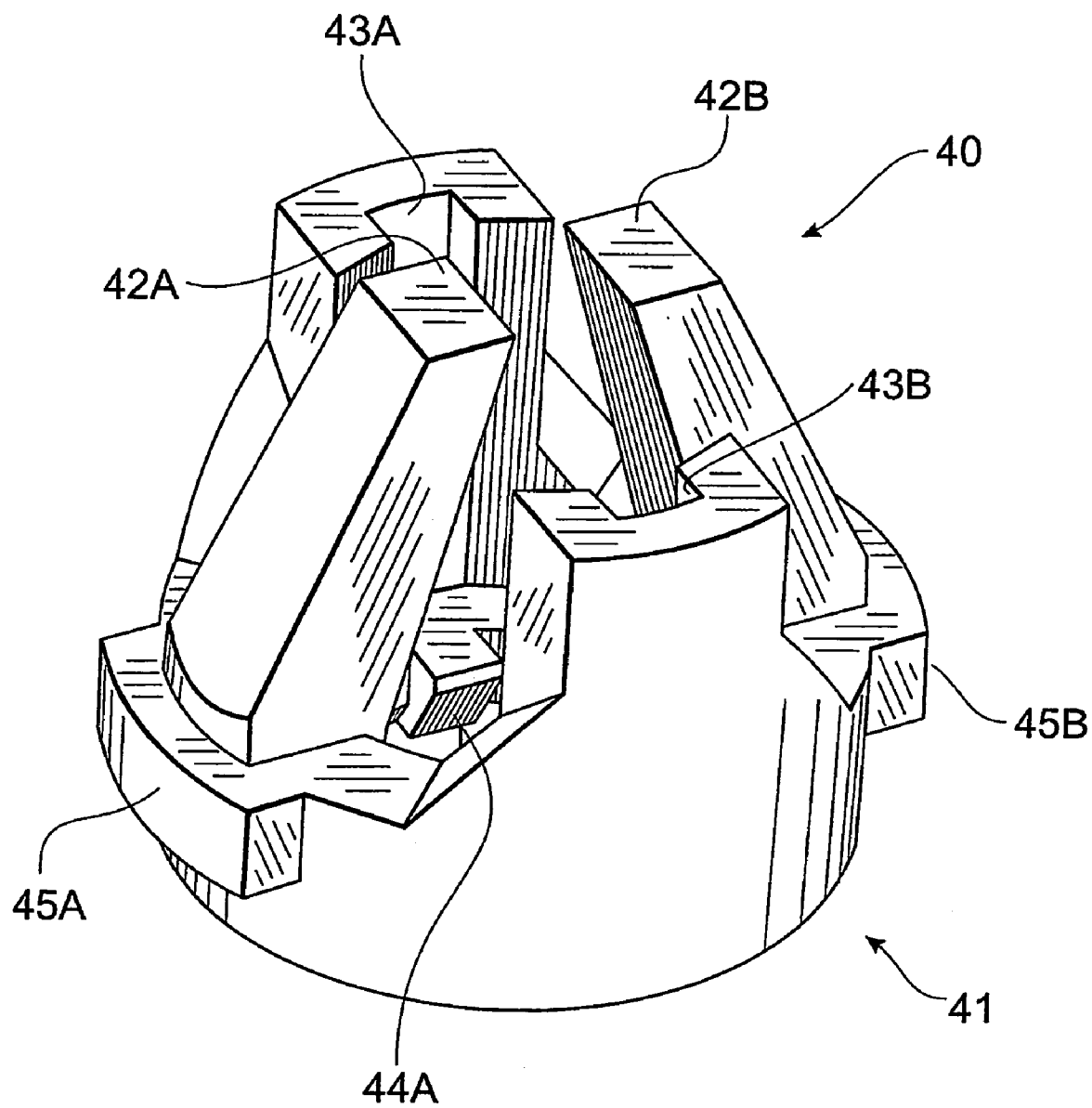
FIG. 3 is a perspective view of an embodiment of an outer member.

Referring now to FIG. 3, outer member 40 comprises outer member body 41 having pawls 42A, 42B, channels 43A, 43B, fingers 44A, 44B and barrel-engaging shoulders 45A, 45B. Pawls 42A, 42B are resiliently deformable from an initial position where engagement with steps 24 is prevented to a position where pawls 42A, 42B can engage steps 24 to prevent, impede or otherwise hinder subsequent plunger 20 withdrawal, as will be described in more detail hereinafter.

Figure 4:
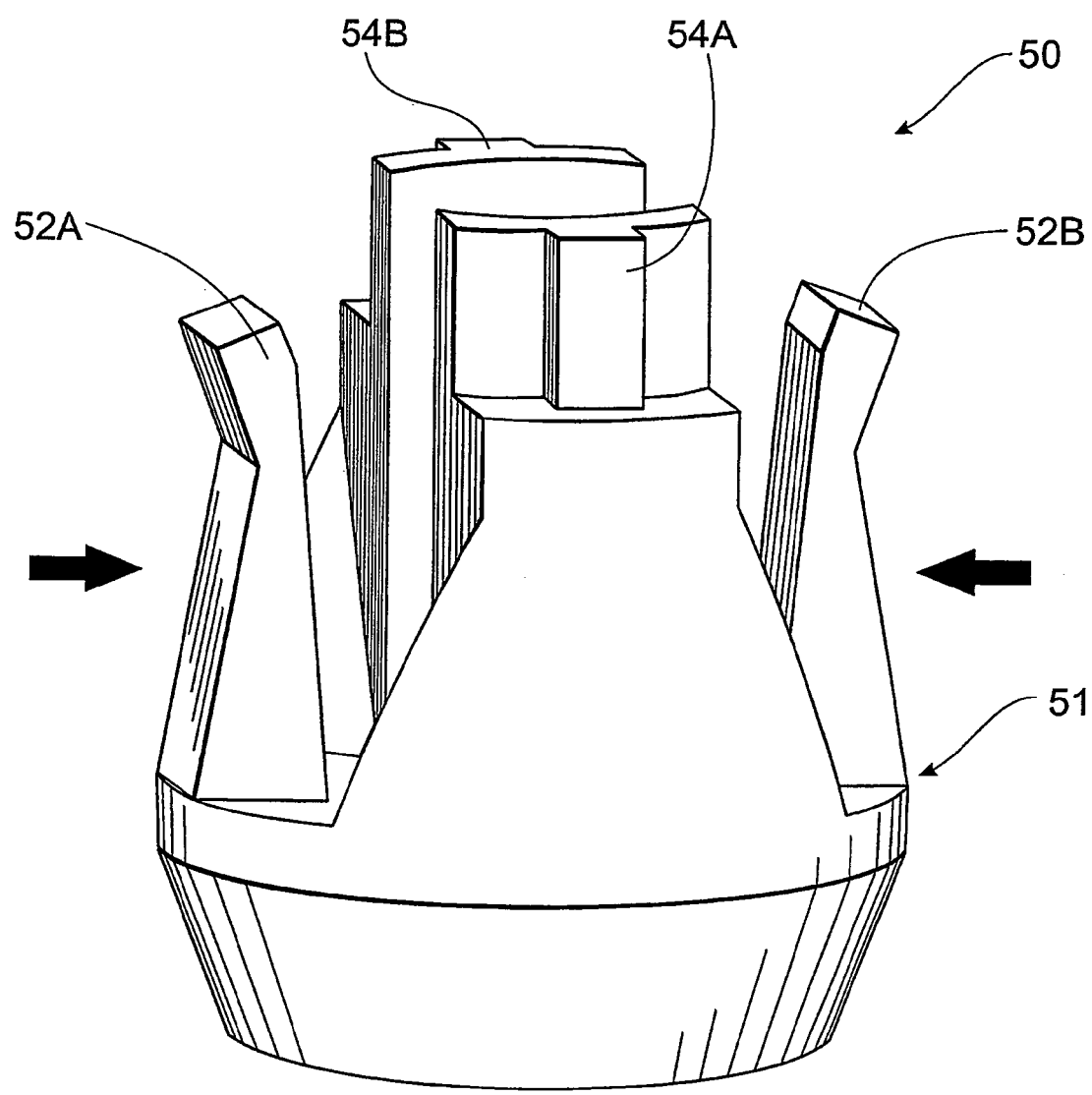
FIG. 4 is a perspective view of an embodiment of an inner member.

As can be seen in FIG. 4, inner member 50 comprises inner member body 51 having first projection 52A and second projection 52B, which projections are resiliently deformable in the direction indicated by arrows. Inner member body 51 also comprises tabs 54A, 54B.

Figure 5:
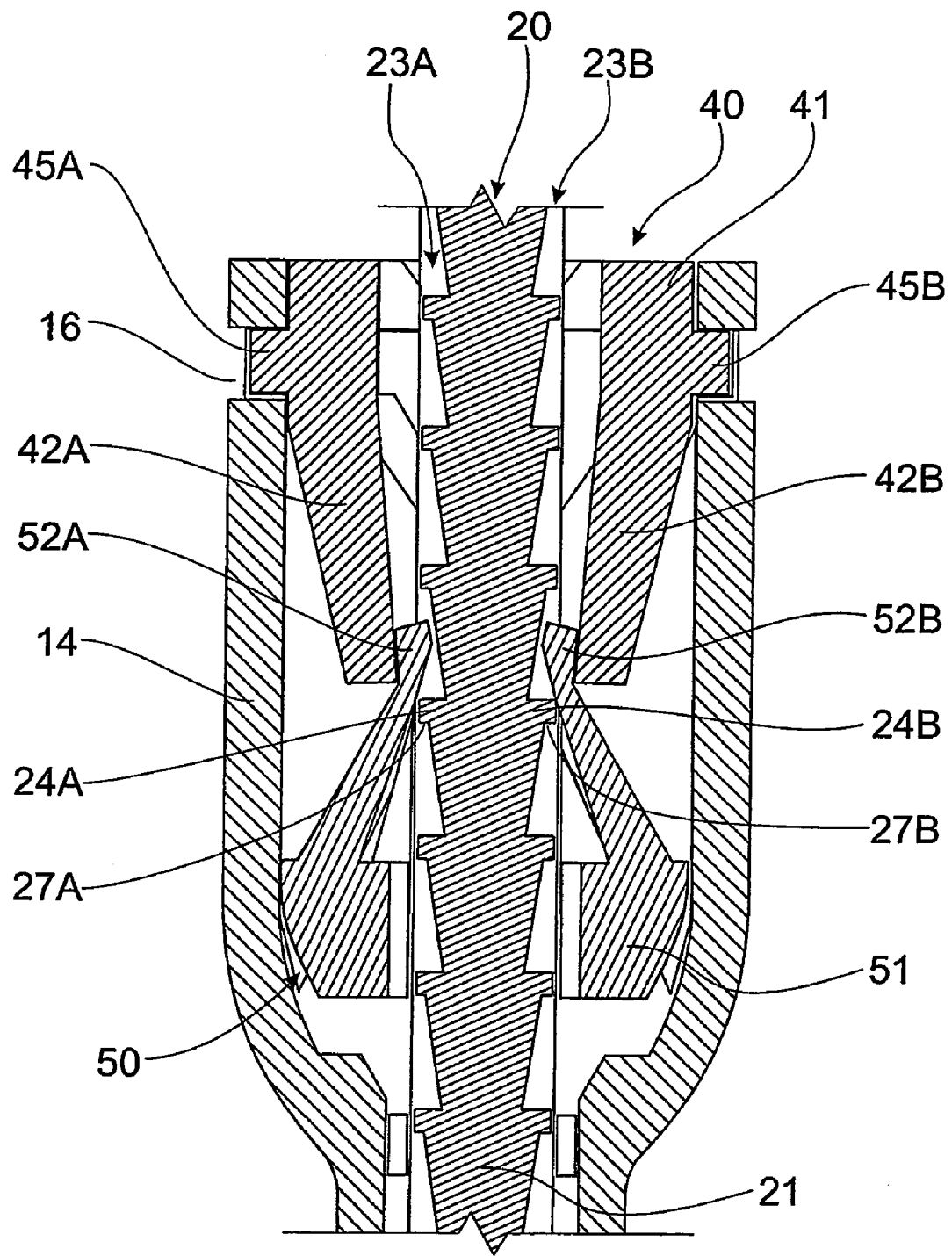
FIG. 5 is a plan view of a longitudinal section through an embodiment of a syringe during plunger withdrawal.

With this in mind and with reference to FIG. 5, when assembled, barrel-engaging shoulders 45A, 45B of outer member 40 fit into respective locating slots 16 of flared plunger end 14 of barrel 11 of syringe 10. Tabs 54A, 54B of inner member 50 (FIG. 4) are slidably located in channels 43A, 43B of outer member 40 (not shown). This aligns inner member 50 and outer member 40, preventing rotation therebetween. Alignment and non-rotation of plunger 20 is facilitated by fingers 44A, 44B of outer member 40 slidably engaging respective, opposed guide slots 28 on plunger rod 21 (not shown).

In this correctly aligned and non-rotatable configuration, first projection 52A and second projection 52B of inner member 50 are initially, respectively positioned between pawls 42A, 42B of outer member 40 and ratchets 23A, 23B, thereby preventing pawls 42A, 42B of collar 40 contacting steps 24A, 24B.

It can be seen that during withdrawal of plunger 20 to fill barrel 11, pawls 42A, 42B tend to exert an inward pressure on projections 52A, 52B thereby clamping projections 52A, 52B in position. Accordingly, projections 52A, 52B pass over respective steps 24A, 24B with minimal interference thereby providing a "smooth" feel during plunger 20 withdrawal.

Referring to FIG. 2 and FIG. 5, fingers 44A, 44B of outer member 40 slidably engage respective, opposed guide slots 28 on plunger rod 21, in use bear against ledges 33 if plunger 20 is withdrawn beyond a certain point to thereby prevent further plunger withdrawal. This prevents complete withdrawal of plunger 20 from barrel 11.

Figure 6:
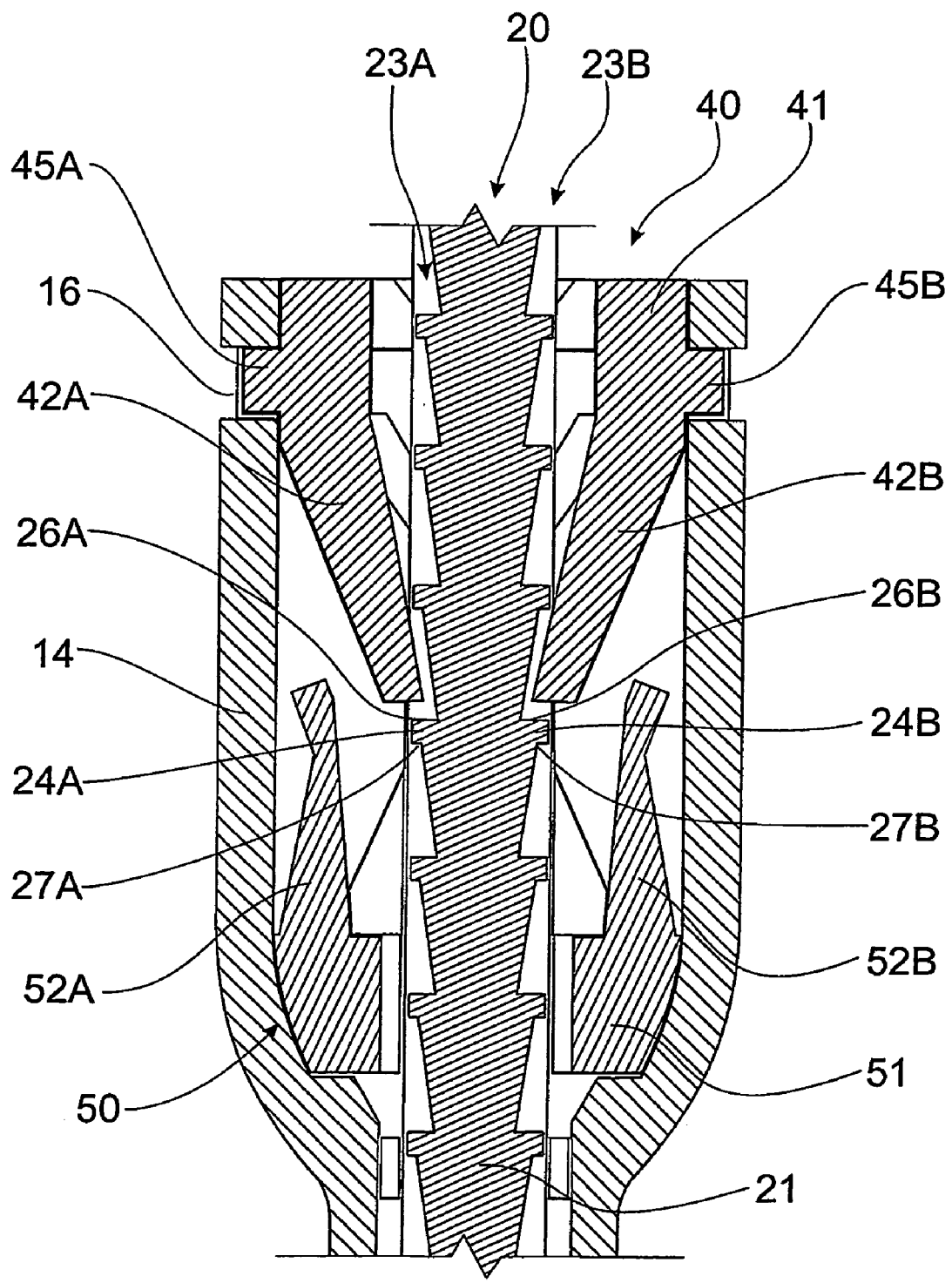
FIG. 6 is a plan view of a longitudinal section through an embodiment of a syringe during plunger depression.

Referring to FIG. 5 and FIG. 6, upon depression of plunger 20, projections 52A, 52B of inner member respectively engage shallow shoulders 27A, 27B of steps 24A, 24B at whichever point has been reached during withdrawal of plunger 20. The force applied to plunger 20 by the user pushes shallow shoulders 27A, 27B of steps 24A, 24B against projections 52A, 52B respectively, thereby forcing inner member 50 out of its initial position engaged with outer member 40 to thereby expose pawls 42A, 42B. It can be seen in FIG. 6 that projections 52A, 52B return to a non-deformed position and no longer contact ratchets 24A, 24B.

Referring again to FIG. 6, due to the respective orientations of pawls 42A, 42B of outer member 40, the direction of inclined surfaces 25A, 25B and the relative shallowness of shallow shoulders 27A, 27B, pawls 42A, 42B do not appreciably interfere with depression of plunger 20 which provides a "smooth" feel to the user during delivery. However, should the user attempt to subsequently withdraw plunger 20 to re-fill syringe 10, pawls 42A, 42B respectively engage deep shoulders 26A, 26B of steps 24A, 24B in ratchets 23A, 23B to thereby prevent withdrawal of plunger 20 and re-use of syringe 10.

In light of the foregoing it will be appreciated that the present invention provides a relatively simple, robust and inexpensive syringe that is automatically disabled with little or no assistance from the user to thereby prevent, or at least minimize the likelihood of, re-use of the syringe.

Furthermore, the invention provides a mechanism for a syringe which can automatically disable the syringe and thereby prevent re-use of the syringe, which mechanism can be utilized with a non-retractable syringe needle.

Throughout the specification, the aim has been to describe the preferred embodiments of the invention without limiting the invention to any one embodiment or specific collection of features. Various changes and modifications may be made to the embodiments described and illustrated without departing from the present invention. In particular, opposed ratchets 23A, 23B need not be located at 180° with respect to each other, but may readily adopt different, relative positions on plunger 20 while performing the same function. Furthermore, the number of ratchets 23 and steps, teeth, ridges or abutments 24 that form the ratchet may be readily modified, as may be the number of pawls 42 on collar 40.

The invention claimed is:

1. A disabling system for a syringe, said disabling system comprising a plunger having at least one ratchet and a collar mountable to a barrel of said syringe, said collar comprising an inner member and an outer member having at least one pawl capable of engaging said ratchet, the inner member comprising one or more resiliently deformable projections initially positioned between the pawl of the outer member and the ratchet to prevent engagement of said ratchet by said at least one pawl until said plunger is depressed forcing the inner member out of engagement with the outer member to allow the pawl of the outer member to engage the ratchet.

2. The disabling system of claim 1, wherein the plunger comprises two opposed ratchets, each disposed longitudinally along said plunger.

3. The disabling system of claim 2, wherein each of said two opposed ratchets are alignable relative to two pawls so as to be capable of engaging said two pawls to prevent withdrawal of said plunger during or following depression of said plunger.

4. The disabling system of claim 3, wherein each of said two opposed ratchets comprise a plurality of aligned steps, teeth or abutments.

5. The disabling system of claim 1, wherein the inner member and the outer member are in use incapable of rotation relative to each other.

6. The disabling system of claim 5, wherein said outer member comprises two fingers capable of slidably engaging respective, opposed guide slots located on said plunger to thereby prevent rotation of said plunger relative to said collar.

7. A syringe comprising a plunger comprising at least one ratchet, a barrel and a collar mountable to said barrel, said collar comprising an inner member and an outer member having at least one pawl, the inner member comprising one or more resiliently deformable projections initially positioned between the pawl of the outer member and the ratchet to prevent engagement of said ratchet by said at least one pawl until said plunger is depressed forcing the inner member out of engagement with the outer member to allow the pawl of the outer member to engage the ratchet.

8. The syringe of claim 7, wherein the collar comprises two pawls.

9. The syringe of claim 8, wherein the plunger comprises two opposed ratchets, each disposed longitudinally along said plunger.

10. The syringe of claim 9, wherein said two opposed ratchets are respectively alignable with the two pawls so as to be capable of respectively engaging said pawls, in use to prevent withdrawal of said plunger during or following depression of said plunger.

11. The syringe of claim 10, wherein each of said two opposed ratchets comprise a plurality of aligned steps, teeth or abutments.

12. The syringe of claim 7, wherein the inner member and the outer member are incapable of rotation relative to each other.

13. The syringe of claim 12, wherein said outer member comprises two fingers that slidably engage respective, opposed guide slots located on said plunger to thereby prevent rotation of said plunger relative to said collar.

14. A syringe comprising:
a barrel that comprises two pawls; and
a plunger comprising:
two opposed ratchets respectively engageable by said two pawls to prevent withdrawal of said plunger during or following depression of said plunger; and
two opposed guide slots;
wherein said barrel comprises a collar having an inner member and an outer member that are incapable of rotation relative to each other, the inner member comprising one or more resiliently deformable projections initially positioned between the pawl of the outer member and the ratchet to prevent engagement of said ratchet by said two pawls until said plunger is depressed forcing the inner member out of engagement with the outer member to allow the pawl of the outer member to engage the ratchet, said outer member comprising said two pawls and further comprising two fingers that respectively slidably engage said opposed guide slots of said plunger to thereby prevent rotation of said plunger relative to said collar.

15. A method of operating a syringe, said method comprising:
providing a syringe comprising a plunger including at least one ratchet, a barrel and a collar mountable to said barrel, said collar comprising an inner member and an outer member having at least one pawl, the inner member comprising one or more resiliently deformable projections initially positioned between the pawl of the outer member and the ratchet to prevent engagement of said ratchet by said two pawls until said plunger is depressed forcing the inner member out of engagement with the outer member to allow the pawl of the outer member to engage the ratchet; and depressing said plunger from a first position at which said at least one pawl is not engageable with said at least one ratchet by at least one projection of the inner member positioned between the at least one pawl and the at least one ratchet to a second position at which said at least one pawl is engageable with said at least one ratchet to prevent withdrawal of said plunger.

16. A method of making a disabling system for a syringe, the method comprising:
forming at least one ratchet on a plunger; and
positioning an inner member of a collar which is mountable to a barrel of a syringe, the inner member comprising one or more resiliently deformable projections initially positioned between the pawl of the outer member and the ratchet to prevent engagement of the at least one ratchet of the plunger by at least one pawl of an outer member of the collar until the plunger is depressed forcing the inner member out of engagement with the outer member to allow the pawl of the outer member to engage the ratchet.

17. The method of claim 16 wherein the forming at least one ratchet on a plunger further comprises forming at least two ratchets which are disposed longitudinally along the plunger.

18. The method of claim 17 further comprising aligning each of the at least two ratchets relative to two of the at least one pawls for engagement following depression of the plunger.

19. The method of claim 18 wherein each of the two ratchets comprise a plurality of at least one of aligned steps, teeth and abutments.

20. The method of claim 16 wherein the inner member and the outer member of the collar are incapable of rotation relative to each other.

21. The method of claim 20 further comprising slidably engaging at least two fingers of the outer member in guide slots located on the plunger to prevent rotation of the plunger relative to the collar.

22. A method of making a syringe, the method comprising:
forming at least one ratchet on a plunger;
mounting a collar in a barrel, the collar comprising an inner member and an outer member having at least one pawl; and
mounting the plunger for movement in the barrel, the inner member comprising one or more resiliently deformable projections initially positioned between the pawl of the outer member and the ratchet to prevent initial engagement of the at least one ratchet by the at least one pawl until the plunger is depressed in the barrel forcing the inner member out of engagement with the outer member to allow the pawl of the outer member to engage the ratchet.

23. The method of claim 22 wherein the outer member has at least two of the pawls.

24. The method of claim 23 wherein the forming at least one ratchet on a plunger further comprises forming at least two ratchets which are disposed longitudinally along the plunger.

25. The method of claim 24 further comprising aligning each of the at least two ratchets relative to two of the at least one pawls for engagement following depression of the plunger.

26. The method of claim 25 wherein each of the two ratchets comprise a plurality of at least one of aligned steps, teeth and abutments.

27. The method of claim 26 wherein the inner member and the outer member are incapable of rotation relative to each other.

28. The method of claim 27 further comprising slidably engaging at least two fingers of the outer member in guide slots located on the plunger to prevent rotation of the plunger relative to the collar.

* * * * *